(12) United States Patent
Fang et al.

(10) Patent No.: US 8,501,726 B2
(45) Date of Patent: Aug. 6, 2013

(54) AZETIDINE DERIVATIVES AS SPHINGOSINE 1-PHOSPHATE (S1P) RECEPTOR MODULATORS

(75) Inventors: Wenkui K. Fang, Irvine, CA (US); Liming Wang, Irvine, CA (US); Evelyn G. Corpuz, Irvine, CA (US); Ken Chow, Newport Coast, CA (US); Wha Bin Im, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 12 days.

(21) Appl. No.: 13/293,687

(22) Filed: Nov. 10, 2011

(65) Prior Publication Data

US 2012/0142663 A1 Jun. 7, 2012

Related U.S. Application Data

(60) Provisional application No. 61/419,293, filed on Dec. 3, 2010.

(51) Int. Cl.
*A61K 31/4245* (2006.01)
*C07D 413/10* (2006.01)

(52) U.S. Cl.
USPC ....... 514/210.18; 514/364; 548/131; 548/953

(58) Field of Classification Search
USPC ...................... 514/210.18, 364; 548/131, 953
See application file for complete search history.

(56) References Cited

FOREIGN PATENT DOCUMENTS

| | | |
|---|---|---|
| GB | 1053825 | 1/1967 |
| WO | WO 03-105771 | 12/2003 |
| WO | WO 2008-076356 | 6/2008 |
| WO | WO 2010-085581 | 7/2010 |
| WO | WO 2010-085584 | 7/2010 |

OTHER PUBLICATIONS

Vippagunta et al., Advanced Drug Delivery Reviews, p. 3-27.*
Chapter 11 of Byrn et al., Solid-State Chemistry of Drugs (2nd Ed. 1999) (pp. 233-247).*
Cross, L.C. et al., Rules for the Nomencalture of Organic Chemistry Section E: Stereochemistry, Pure Appli. Chem., 45, 11-30 (1976).
Hale, Jeffrey et al., Potent S1P Receptor Agonists Replicate the Pharmacologic Actions of the Novel Immune Modulator FTY720, Bioorg. & Med. Chem. Lett. 14, 3351-3355 (2004).
Li, Zhen et al., "Discovery of Potent 3,5-Diphenyl-1,2,4-Oxadiazole Sphingosine-1-Phosphate-1 (S1P1) Receptor Agonists With Exceptional Selectivity Against S1P2 and S1P3", J. Med. Chem., vol. 48, Iss. 20, pp. 6169-6173 (2005).
Schurer, S.C. et al., "Ligand-Binding Pocket Shape Differences Between Sphingosine 1-Phosphate (S1P) Receptors S1P1 and S1P3 Determine Efficiency of Chemical Probe identification by Ultrahigh-Thoughput Screening", ACS Chemical Biology, vol. 3, No. 8, 486-498, Aug. 2008.
Stahl, Heinrich et al., Handbook of Pharmaceutical Salts, Verlag Helvetica Chimica Acta—Zurich, 329-345 (2002).
Vaccaro, Wayne et al., "Inhibitors of Acyl CoA:Cholesterol Acyltransferase." Journal of Medicinal Chemistry, 39(8), 1704-1719 (1996).

* cited by examiner

*Primary Examiner* — Yong Chu
(74) *Attorney, Agent, or Firm* — Doina G. Ene

(57) ABSTRACT

The present invention relates to novel azetidine derivatives, processes for preparing them, pharmaceutical compositions containing them and their use as pharmaceuticals as modulators of sphingosine-1-phosphate receptors.

8 Claims, No Drawings ic
AZETIDINE DERIVATIVES AS SPHINGOSINE 1-PHOSPHATE (S1P) RECEPTOR MODULATORS

CROSS REFERENCE TO RELATED APPLICATIONS

This application claims the benefit of U.S. Provisional Application Ser. No. 61/419,293 filed Dec. 3, 2010, which is hereby incorporated by reference in its entirety.

FIELD OF THE INVENTION

The present invention relates to novel azetidine derivatives, processes for preparing them, pharmaceutical compositions containing them and their use as pharmaceuticals, as modulators of sphingosine-1-phosphate receptors. The invention relates specifically to the use of these compounds and their pharmaceutical compositions to treat disorders associated with sphingosine-1-phosphate (S1P) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

SUMMARY OF THE INVENTION

A group of novel of azetidine derivatives which are potent and selective sphingosine-1-phosphate modulators has been discovered. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This invention describes compounds of Formula I, which have sphingosine-1-phosphate receptor biological activity. The compounds in accordance with the present invention are thus of use in medicine, for example in the treatment of humans with diseases and conditions that are alleviated by S1P modulation.

In one aspect, the invention provides a compound having Formula I or a pharmaceutically acceptable salt thereof or a stereoisomer thereof, or the geometrical isomers, enantiomers, diastereoisomers, tautomers, zwitterions or a pharmaceutically acceptable salt thereof:

Formula I wherein:

A is $C_{6-10}$ aryl, heterocycle, $C_{3-8}$ cycloalkyl or $C_{3-8}$ cycloalkenyl;

B is $C_{6-10}$ aryl, heterocycle, $C_{3-8}$ cycloalkyl or $C_{3-8}$ cycloalkenyl;

$R^1$ is H, halogen, $-OC_{1-8}$ alkyl, $C_{1-8}$ alkyl, CN, $C(O)R^9$, $NR^{10}R^{11}$ or hydroxyl;

$R^2$ is H, halogen, $-OC_{1-8}$ alkyl, $C_{1-8}$ alkyl, CN, $C(O)R^9$, $NR^{10}R^{11}$ or hydroxyl;

$R^3$ is H, halogen, $-OC_{1-8}$ alkyl, $C_{1-8}$ alkyl, CN, $C(O)R^9$, $NR^{10}R^{11}$ or hydroxyl;

$R^4$ is H, halogen, $-OC_{1-8}$ alkyl, $C_{1-8}$ alkyl, CN, $C(O)R^9$, $NR^{10}R^{11}$ or hydroxyl;

$R^5$ is H, halogen, $-OC_{1-8}$ alkyl, $C_{1-8}$ alkyl, CN, $C(O)R^9$, $NR^{10}R^{11}$ or hydroxyl;

$R^6$ is H, halogen, $-OC_{1-8}$ alkyl, $C_{1-8}$ alkyl, CN, $C(O)R^9$, $NR^{10}R^{11}$ or hydroxyl;

$R^7$ is H, halogen, $-OC_{1-8}$ alkyl, $C_{1-8}$ alkyl, CN, $C(O)R^9$, $NR^{10}R^{11}$ or hydroxyl;

$R^8$ is halogen, $-OC_{1-8}$ alkyl, $C_{1-8}$ alkyl, CN, $C(O)R^9$, $NR^{10}R^{11}$ or hydroxyl;

L is O, S, NH or $CH_2$;

$R^9$ is H, hydroxyl or $C_{1-8}$ alkyl;

$R^{10}$ is H or $C_{1-8}$ alkyl;

$R^{11}$ is H or $C_{1-8}$ alkyl; and a is 0 or 1.

In another aspect, the invention provides a compound having Formula I wherein L is O, S or NH.

In another aspect, the invention provides a compound having Formula I wherein L is O.

In another aspect, the invention provides a compound having Formula I wherein L is S.

In another aspect, the invention provides a compound having Formula I wherein L is NH.

In another aspect, the invention provides a compound having Formula I wherein

A is $C_6$ aryl;

B is $C_6$ aryl;

$R^1$ is H, halogen, $-OC_{1-6}$ alkyl, $C_{1-6}$ alkyl, CN, $C(O)R^9$, $NR^{10}R^{11}$ or hydroxyl;

$R^2$ is H, halogen, $-OC_{1-6}$ alkyl, $C_{1-6}$ alkyl, CN, $C(O)R^9$, $NR^{10}R^{11}$ or hydroxyl;

$R^3$ is H, halogen, $-OC_{1-6}$ alkyl, $C_{1-6}$ alkyl, CN, $C(O)R^9$, $NR^{10}R^{11}$ or hydroxyl;

$R^4$ is H, halogen, $-OC_{1-6}$ alkyl, $C_{1-6}$ alkyl, CN, $C(O)R^9$, $NR^{10}R^{11}$ or hydroxyl;

$R^5$ is H, halogen, $-OC_{1-6}$ alkyl, $C_{1-6}$ alkyl, CN, $C(O)R^9$, $NR^{10}R^{11}$ or hydroxyl;

$R^6$ is H, halogen, $-OC_{1-6}$ alkyl, $C_{1-6}$ alkyl, CN, $C(O)R^9$, $NR^{10}R^{11}$ or hydroxyl;

$R^7$ is H, halogen, —$OC_{1-6}$ alkyl, $C_{1-6}$ alkyl, CN, $C(O)R^9$, $NR^{10}R^{11}$ or hydroxyl;
$R^8$ is halogen, —$OC_{1-6}$ alkyl, $C_{1-6}$ alkyl, CN, $C(O)R^9$, $NR^{10}R^{11}$ or hydroxyl;
L is O, S or NH;
$R^9$ is H, hydroxyl or $C_{1-6}$ alkyl;
$R^{10}$ is H or $C_{1-6}$ alkyl;
$R^{11}$ is H or $C_{1-6}$ alkyl; and
a is 0 or 1.

In another aspect, the invention provides a compound having Formula I wherein

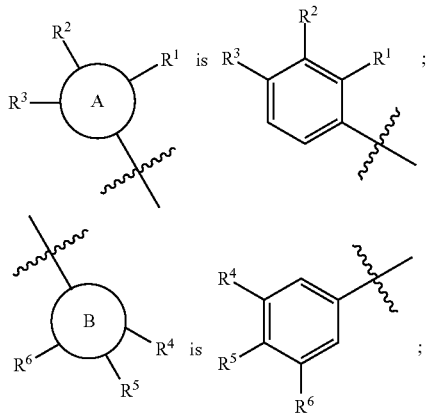

$R^1$ is H or halogen;
$R^2$ is H or halogen;
$R^3$ is H or halogen;
$R^4$ is H or $C_{1-6}$ alkyl,
$R^5$ is H or $C_{1-6}$ alkyl;
$R^6$ is H or $C_{1-6}$ alkyl;
$R^7$ is H;
a is 0; and
L is O, S or NH.

In another aspect, the invention provides a compound having Formula I wherein

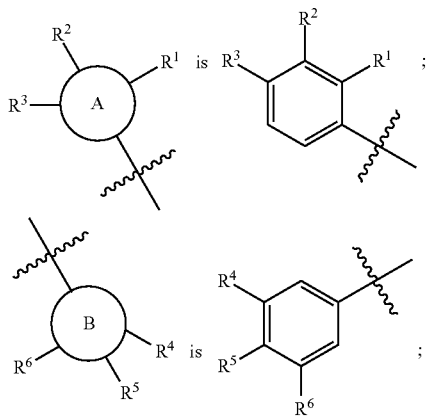

$R^1$ is H or halogen;
$R^2$ is H or halogen;
$R^3$ is H or halogen;
$R^4$ is H or $C_{1-6}$ alkyl,
$R^5$ is H or $C_{1-6}$ alkyl;
$R^6$ is H or $C_{1-6}$ alkyl;
$R^7$ is H;
a is 0; and
L is O.

In another aspect, the invention provides a compound having Formula I wherein

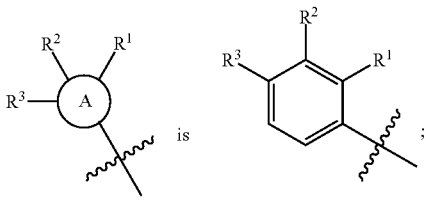

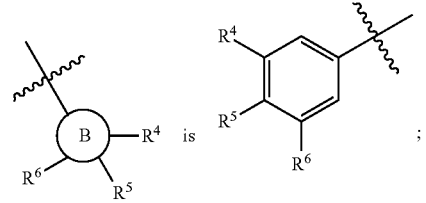

$R^1$ is H or halogen;
$R^2$ is H or halogen;
$R^3$ is H or halogen;
$R^4$ is H or $C_{1-6}$ alkyl,
$R^5$ is H or $C_{1-6}$ alkyl;
$R^6$ is H or $C_{1-6}$ alkyl;
$R^7$ is H;
a is 0; and
L is S.

In another aspect, the invention provides a compound having Formula I wherein

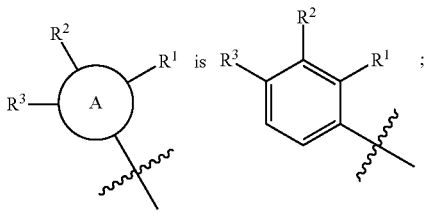

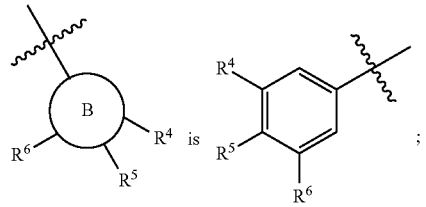

$R^1$ is H or halogen;
$R^2$ is H or halogen;
$R^3$ is H or halogen;
$R^4$ is H or $C_{1-6}$ alkyl,
$R^5$ is H or $C_{1-6}$ alkyl;
$R^6$ is H or $C_{1-6}$ alkyl;
$R^7$ is H;
a is 0; and
L is NH.

In another embodiment, the invention provides a compound having Formula I wherein:

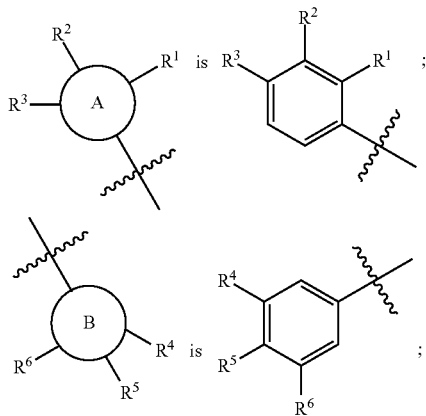

R$^1$ is H, halogen, —OC$_{1-6}$ alkyl, C$_{1-6}$ alkyl, CN, C(O)R$^9$, NR$^{10}$R$^{11}$ or hydroxyl;
R$^2$ is H, halogen, —OC$_{1-6}$ alkyl, C$_{1-6}$ alkyl, CN, C(O)R$^9$, NR$^{10}$R$^{11}$ or hydroxyl;
R$^3$ is H, halogen, —OC$_{1-6}$ alkyl, C$_{1-6}$ alkyl, CN, C(O)R$^9$, NR$^{10}$R$^{11}$ or hydroxyl;
R$^4$ is H, halogen, —OC$_{1-6}$ alkyl, C$_{1-6}$ alkyl, CN, C(O)R$^9$, NR$^{10}$R$^{11}$ or hydroxyl;
R$^5$ is H, halogen, —OC$_{1-6}$ alkyl, C$_{1-6}$ alkyl, CN, C(O)R$^9$, NR$^{10}$R$^{11}$ or hydroxyl;
R$^6$ is H, halogen, —OC$_{1-6}$ alkyl, C$_{1-6}$ alkyl, CN, C(O)R$^9$, NR$^{10}$R$^{11}$ or hydroxyl;
R$^7$ is H, halogen, —OC$_{1-6}$ alkyl, C$_{1-6}$ alkyl, CN, C(O)R$^9$, NR$^{10}$R$^{11}$ or hydroxyl;
R$^8$ is halogen, —OC$_{1-6}$ alkyl, C$_{1-6}$ alkyl, CN, C(O)R$^9$, NR$^{10}$R$^{11}$ or hydroxyl;
L is O, S or NH;
R$^9$ is H, hydroxyl or C$_{1-6}$ alkyl;
R$^{10}$ is H or C$_{1-6}$ alkyl;
R$^{11}$ is H or C$_{1-6}$ alkyl; and
a is 0 or 1.

In another embodiment, the invention provides a compound having Formula I wherein:

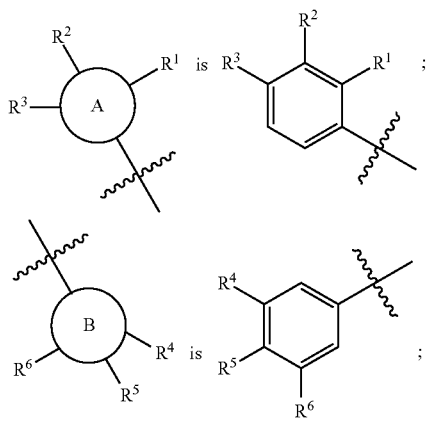

R$^1$ is H or chloro;
R$^2$ is H or chloro,
R$^3$ is H;
R$^4$ is H, ethyl, propyl or methyl;
R$^5$ is H, ethyl, propyl or methyl;
R$^6$ is H, ethyl, propyl or methyl;
R$^7$ is H;
a is 0; and
L is O, S or NH.

In another embodiment, the invention provides a compound having Formula I wherein:

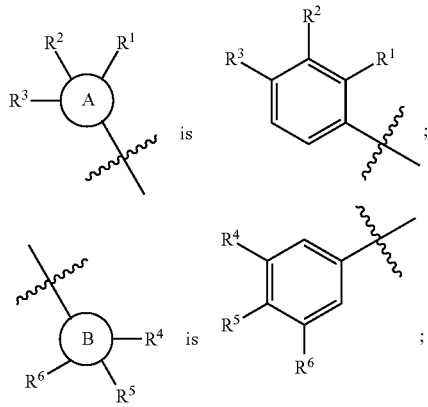

R$^1$ is H, chloro;
R$^2$ is H, chloro;
R$^3$ is H;
R$^4$ is H or methyl;
R$^5$ is H, ethyl, propyl or methyl;
R$^6$ is H;
R$^7$ is H;
a is 0; and
L is O, S or NH.

In another embodiment, the invention provides a compound having Formula I wherein:

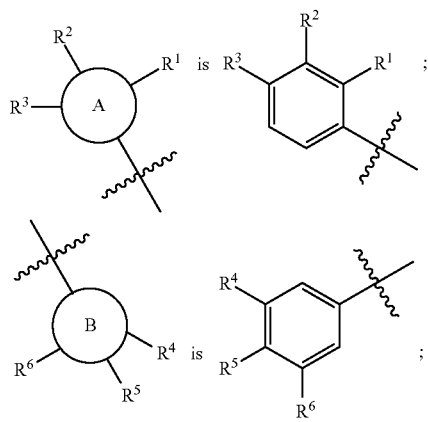

R$^1$ is H, chloro;
R$^2$ is H, chloro;
R$^3$ is H;
R$^4$ is H or methyl;
R$^5$ is H, ethyl, propyl or methyl;
R$^6$ is H;
R$^7$ is H;
a is 0; and
L is O.

In another embodiment, the invention provides a compound having Formula I wherein:

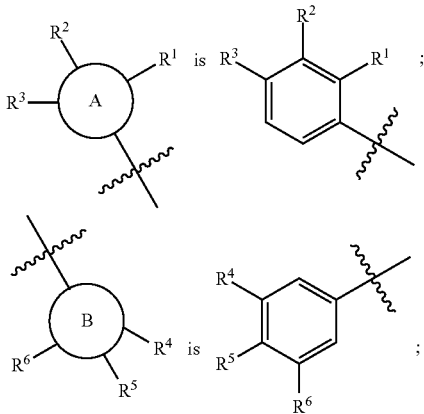

R¹ is H;
R² is H, chloro;
R³ is H;
R⁴ is methyl;
R⁵ is methyl;
R⁶ is H;
R⁷ is H;
a is 0; and
L is NH.

In another embodiment, the invention provides a compound having Formula I wherein:

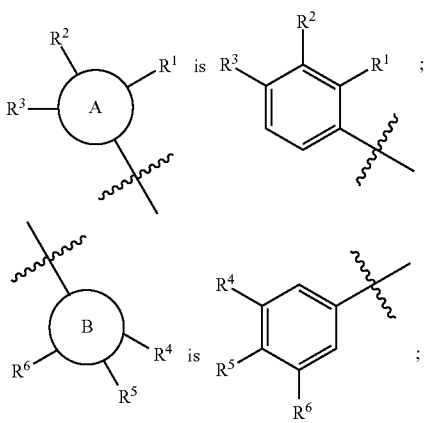

$R^1$ is H, halogen, —$OC_{1-6}$ alkyl, $C_{1-6}$ alkyl, CN, $C(O)R^9$, $NR^{10}R^{11}$ or hydroxyl;
$R^2$ is H, halogen, —$OC_{1-6}$ alkyl, $C_{1-6}$ alkyl, CN, $C(O)R^9$, $NR^{10}R^{11}$ or hydroxyl;
$R^3$ is H, halogen, —$OC_{1-6}$ alkyl, $C_{1-6}$ alkyl, CN, $C(O)R^9$, $NR^{10}R^{11}$ or hydroxyl;
$R^4$ is H, halogen, —$OC_{1-6}$ alkyl, $C_{1-6}$ alkyl, CN, $C(O)R^9$, $NR^{10}R^{11}$ or hydroxyl;
$R^5$ is H, halogen, —$OC_{1-6}$ alkyl, $C_{1-6}$ alkyl, CN, $C(O)R^9$, $NR^{10}R^{11}$ or hydroxyl;
$R^6$ is H, halogen, —$OC_{1-6}$ alkyl, $C_{1-6}$ alkyl, CN, $C(O)R^9$, $NR^{10}R^{11}$ or hydroxyl;
$R^7$ is H, halogen, —$OC_{1-6}$ alkyl, $C_{1-6}$ alkyl, CN, $C(O)R^9$, $NR^{10}R^{11}$ or hydroxyl;
$R^8$ is halogen, —$OC_{1-6}$ alkyl, $C_{1-6}$ alkyl, CN, $C(O)R^9$, $NR^{10}R^{11}$ or hydroxyl;
L is O;
$R^9$ is H, hydroxyl or $C_{1-6}$ alkyl;
$R^{10}$ is H or $C_{1-6}$ alkyl;
$R^{11}$ is H or $C_{1-6}$ alkyl; and
a is 0 or 1.

In another embodiment, the invention provides a compound having Formula I wherein:

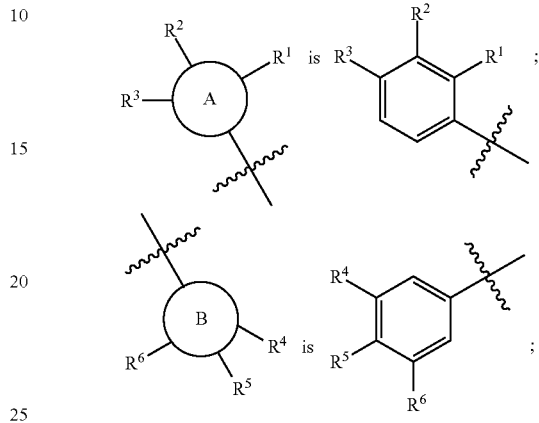

$R^1$ is H, halogen, —$OC_{1-6}$ alkyl, $C_{1-6}$ alkyl, CN, $C(O)R^9$, $NR^{10}R^{11}$ or hydroxyl;
$R^2$ is H, halogen, —$OC_{1-6}$ alkyl, $C_{1-6}$ alkyl, CN, $C(O)R^9$, $NR^{10}R^{11}$ or hydroxyl;
$R^3$ is H, halogen, —$OC_{1-6}$ alkyl, $C_{1-6}$ alkyl, CN, $C(O)R^9$, $NR^{10}R^{11}$ or hydroxyl;
$R^4$ is H, halogen, —$OC_{1-6}$ alkyl, $C_{1-6}$ alkyl, CN, $C(O)R^9$, $NR^{10}R^{11}$ or hydroxyl;
$R^5$ is H, halogen, —$OC_{1-6}$ alkyl, $C_{1-6}$ alkyl, CN, $C(O)R^9$, $NR^{10}R^{11}$ or hydroxyl;
$R^6$ is H, halogen, —$OC_{1-6}$ alkyl, $C_{1-6}$ alkyl, CN, $C(O)R^9$, $NR^{10}R^{11}$ or hydroxyl;
$R^7$ is H, halogen, —$OC_{1-6}$ alkyl, $C_{1-6}$ alkyl, CN, $C(O)R^9$, $NR^{10}R^{11}$ or hydroxyl;
$R^8$ is halogen, —$OC_{1-6}$ alkyl, $C_{1-6}$ alkyl, CN, $C(O)R^9$, $NR^{10}R^{11}$ or hydroxyl;
L is NH;
$R^9$ is H, hydroxyl or $C_{1-6}$ alkyl;
$R^{10}$ is H or $C_{1-6}$ alkyl;
$R^{11}$ is H or $C_{1-6}$ alkyl; and
a is 0 or 1.

The term "alkyl", as used herein, refers to saturated, monovalent hydrocarbon moieties having linear or branched moieties or combinations thereof and containing 1 to 6 carbon atoms. One methylene (—$CH_2$—) group, of the alkyl can be replaced by oxygen, sulfur, sulfoxide, nitrogen, carbonyl, carboxyl, sulfonyl, or by a divalent $C_{3-6}$ cycloalkyl. Alkyl groups can be substituted by halogen, hydroxyl, cycloalkyl, amino, non-aromatic heterocycles, carboxylic acid, phosphonic acid groups, sulphonic acid groups, phosphoric acid.

The term "cycloalkyl", as used herein, refers to a monovalent or divalent group of 3 to 8 carbon atoms, derived from a saturated cyclic hydrocarbon. Cycloalkyl groups can be monocyclic or polycyclic. Cycloalkyl can be substituted by alkyl groups or halogen atoms.

The term "cycloalkenyl", as used herein, refers to a monovalent or divalent group of 3 to 8 carbon atoms, derived from a saturated cycloalkyl having one double bond. Cycloalkenyl groups can be monocyclic or polycyclic. Cycloalkenyl groups can be substituted by alkyl groups or halogen atoms.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by alkyl groups.

The term "alkynyl", as used herein, refers to a monovalent or divalent hydrocarbon radical having 2 to 6 carbon atoms, derived from a saturated alkyl, having at least one triple bond. Alkynyl groups can be substituted by alkyl groups.

The term "heterocycle" as used herein, refers to a 3 to 10 membered ring, which can be aromatic or non-aromatic, saturated or non-saturated, containing at least one heteroatom selected form O or N or S or combinations of at least two thereof, interrupting the carbocyclic ring structure. The heterocyclic ring can be interrupted by a C=O; the S heteroatom can be oxidized. Heterocycles can be monocyclic or polycyclic. Heterocyclic ring moieties can be substituted by hydroxyl, alkyl or halogen atoms.

The term "aryl" as used herein, refers to an organic moiety derived from an aromatic hydrocarbon consisting of a ring containing 6 to 10 carbon atoms by removal of one hydrogen. Aryl groups can be monocyclic or polycyclic. Aryl can be substituted by halogen atoms, $-OC_{1-6}$ alkyl, $C_{1-6}$ alkyl, CN, $C(O)(C_{1-6}$ alkyl), $N(C_{1-6}$ alkyl) $(C_{1-6}$ alkyl) or $NH_2$ or $NH(C_{1-6}$ alkyl) or hydroxyl groups. Usually aryl is phenyl.

The term "hydroxyl" as used herein, represents a group of formula "—OH".

The term "carbonyl" as used herein, represents a group of formula "—C(O)".

The term "carboxyl" as used herein, represents a group of formula "—C(O)O—".

The term "sulfonyl" as used herein, represents a group of formula "—SO$_2$".

The term "sulfate" as used herein, represents a group of formula "—O—S(O)$_2$—O—".

The term "carboxylic acid" as used herein, represents a group of formula "—C(O)OH".

The term "sulfoxide" as used herein, represents a group of formula "—S=O".

The term "phosphonic acid" as used herein, represents a group of formula "—P(O)(OH)$_2$".

The term "phosphoric acid" as used herein, represents a group of formula "—(O)P(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Some compounds of the invention are:
1-(4-{5-[(3-chlorophenyl)(4-ethylphenoxy)methyl]-1,2,4-oxadiazol-3-yl}benzyl)azetidine-3-carboxylic acid;
1-(4-{5-[(3-chlorophenyl)(3,4-dimethylphenoxy)methyl]-1,2,4-oxadiazol-3-yl}benzyl)azetidine-3-carboxylic acid;
1-(4-{5-[(3-chlorophenyl)(4-propylphenoxy)methyl]-1,2,4-oxadiazol-3-yl}benzyl)azetidine-3-carboxylic acid;
1-(4-{5-[(2-chlorophenyl)(3,4-dimethylphenoxy)methyl]-1,2,4-oxadiazol-3-yl}benzyl)azetidine-3-carboxylic acid;
1-(4-{5-[(3-chlorophenyl)(4-methylphenoxy)methyl]-1,2,4-oxadiazol-3-yl}benzyl)azetidine-3-carboxylic acid;
1-[4-(5-{(3-chlorophenyl)[(3,4-dimethylphenyl)amino]methyl}-1,2,4-oxadiazol-3-yl)benzyl]azetidine-3-carboxylic acid.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta—Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation.

Therapeutic utilities of S1P modulators are:
Ocular Diseases: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis;

Systemic vascular barrier related diseases: various inflammatory diseases, including acute lung injury, its prevention, sepsis, tumor metastasis, atherosclerosis, pulmonary edemas, and ventilation-induced lung injury;

Autoimmune diseases and immnuosuppression: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation;

Allergies and other inflammatory diseases: urticaria, bronchial asthma, and other airway inflammations including pulmonary emphysema and chronic obstructive pulmonary diseases;

Cardiac functions: bradycardia, congestional heart failure, cardiac arrhythmia, prevention and treatment of atherosclerosis, and ischemia/reperfusion injury;

Wound Healing: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries;

Bone formation: treatment of osteoporosis and various bone fractures including hip and ankles;

Anti-nociceptive activity: visceral pain, pain associated with diabetic neuropathy, rheumatoid arthritis, chronic knee and joint pain, tendonitis, osteoarthritis, neuropathic pains;

Anti-fibrosis: ocular, cardiac, hepatic and pulmonary fibrosis, proliferative vitreoretinopathy, cicatricial pemphigoid, surgically induced fibrosis in cornea, conjunctiva and tenon;

Pains and anti-inflammation: acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains;

CNS neuronal injuries: Alzheimer's disease, age-related neuronal injuries;

Organ transplants: renal, corneal, cardiac and adipose tissue transplants.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of:

Ocular Diseases: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis;

Systemic vascular barrier related diseases: various inflammatory diseases, including acute lung injury, its prevention, sepsis, tumor metastasis, atherosclerosis, pulmonary edemas, and ventilation-induced lung injury;

Autoimmune diseases and immnuosuppression: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation;

Allergies and other inflammatory diseases: urticaria, bronchial asthma, and other airway inflammations including pulmonary emphysema and chronic obstructive pulmonary diseases;

Cardiac functions: bradycardia, congestional heart failure, cardiac arrhythmia, prevention and treatment of atherosclerosis, and ischemia/reperfusion injury;

Wound Healing: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries, rosacea;

Bone formation: treatment of osteoporosis and various bone fractures including hip and ankles;

Anti-nociceptive activity: visceral pain, pain associated with diabetic neuropathy, rheumatoid arthritis, chronic knee and joint pain, tendonitis, osteoarthritis, neuropathic pains;

Anti-fibrosis: ocular, cardiac, hepatic and pulmonary fibrosis, proliferative vitreoretinopathy, cicatricial pemphigoid, surgically induced fibrosis in cornea, conjunctiva and tenon;

Pains and anti-inflammation: acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains;

CNS neuronal injuries: Alzheimer's disease, age-related neuronal injuries;

Organ transplants: renal, corneal, cardiac and adipose tissue transplants.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of Formula I according to the invention can be prepared analogously to conventional methods as understood by the person skilled in the art of synthetic organic chemistry. The synthetic schemes set forth below, illustrate how compounds according to the invention can be made.

The following abbreviations are used in the general scheme and in the specific examples:
CDI 1,1'-Carbonyldiimidazole
THF tetrahydrofuran
RT room temperature
MPLC medium pressure liquid chromatography
NMO 4-Methylmorpholine N-oxide
AcCN 1'1-Azobis(Cyclohexane-1-Carbonitrile)
DCM dichloromethane
TPAP Tetrapropylammonium perruthenate
MeOH methanol
NaCNBH$_3$ sodium cyanoborohydride
H$_2$O water
CD$_3$OD deuterated methanol
MgCl$_2$ magnesium chloride
NaCl sodium chloride
DMSO-d6 deuterated dimethyl sulfoxide A solution of substituted carboxylic acid and CDI in THF was stirred at RT for 30 min., N-Hydroxy-4-(hydroxymethyl)benzamidine (prepared according to Li, Zhen et al, *J. Med. Chem.*, 2005, 48 (20), pp 6169-6173) was added and the resulting solution and stirred at RT overnight. The acid was prepared according to Vaccaro, Wayne; Amore, Cindy; Berger, Joel; Burlier, Robert; Ciader, John; et al. *Journal of Medicinal Chemistry*, 1996, 39(8), 1704-1719. The reaction solution was then transferred to a microwave suitable reaction vessel and heated to 150° C. for 20 min under microwave condition. After cooling to RT, the solvent was removed under reduced pressure. The alcohol was isolated by MPLC using 5 to 10% ethyl acetate in hexane.

Formula I

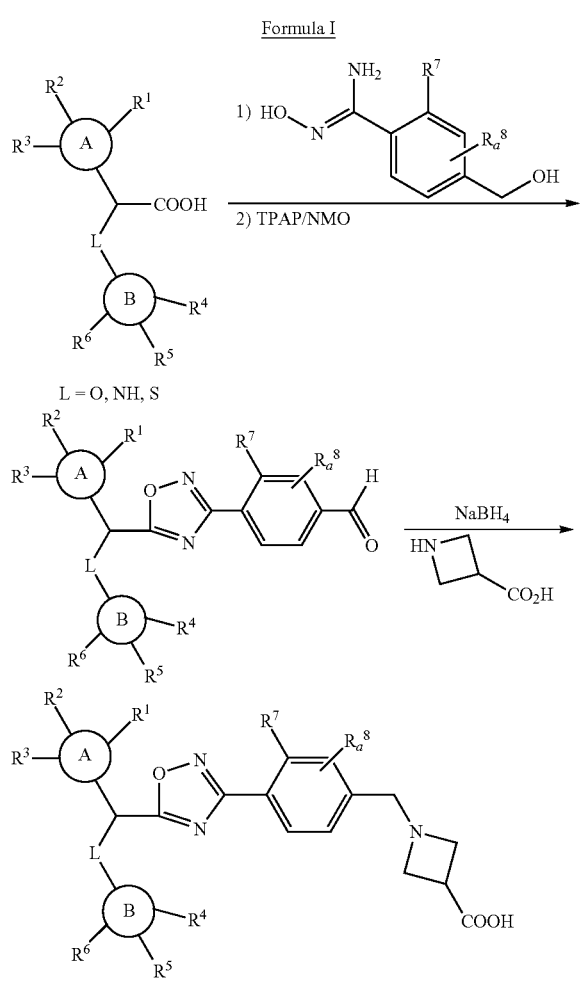

L = O, NH, S

The alcohol was mixed with NMO, molecular sieve in AcCN and DCM. A catalytic amount of TPAP was added. The resulting reaction mixture was stirred at RT for 1 hour and evaporated to dryness. The aldehyde was purified by MPLC using 0-10% ethyl acetate in hexane. The aldehyde intermediate, 3-azetidinecarboxylic acid and TEA were mixed with MeOH. Upon stirring at 60° C. for 90 min, the reaction solution was cooled to RT. NaBH$_4$ was added and stirred at RT for 2 hour. In some cases acetic acid and NaCNBH$_3$ were used. The reaction was quenched with 0.5 mL of water and concentrated to minimal amount. The compound of Formula I was isolated by reverse phase MPLC using H$_2$O in AcCN.

Those skilled in the art will be able to routinely modify and/or adapt the following scheme to synthesize any compounds of the invention covered by Formula I.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names were generated with ACD version 8. In general, characterization of the compounds is performed according to the following methods:

Proton nuclear magnetic resonance ($^1$H NMR) spectra were recorded on a Varian 300 or 600 MHz spectrometer in deuterated solvent. Chemical shifts were reported as δ (delta) values in parts per million (ppm) relative to tetramethylsilane (TMS) as an internal standard (0.00 ppm) and multiplicities were reported as s, singlet; d, doublet; t, triplet; q, quartet; m, multiplet; br, broad. Data were reported in the following format: chemical shift (multiplicity, coupling constant(s) J in hertz (Hz), integrated intensity).

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on an Teledyne-ISCO CombiFlash with a silica column, unless noted otherwise.

Example 1

Compound 1

1-(4-{5-[(3-chlorophenyl)(4-ethylphenoxy)methyl]-1,2,4-oxadiazol-3-yl}benzyl)azetidine-3-carboxylic acid

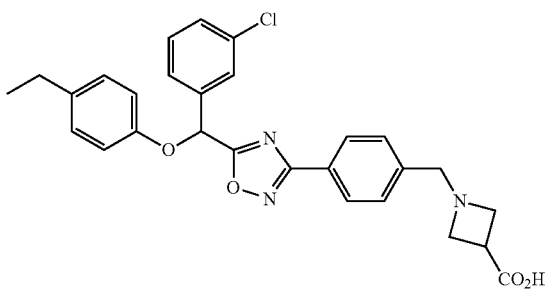 [SMILES: CCc1ccc(OC(c2cccc(Cl)c2)c2nc(-c3ccc(CN4CC(C(=O)O)C4)cc3)no2)cc1]

A solution of 100 mg of 4-{5-[(3-chlorophenyl)(4-ethylphenoxy)methyl]-1,2,4-oxadiazol-3-yl}benzaldehyde,), 3-azetidinecarboxylic acid (24.0 mg, 1.0 eq), and TEA (0.1 ml, 0.7 mmol) was mixed with MeOH (10 ml). Then HOAc (5 drops) and NaCNBH$_3$ (15.0 mg, 1.0 eq) in MeOH/CH$_2$Cl$_2$ were added and gave Compound 1.

$^1$H NMR (300 MHz, CDCl$_3$) δ ppm 1.17 (t, J=7.62 Hz, 3H) 2.56 (q, J=7.42 Hz, 2 H) 3.36 (br. s., 1H) 3.77-4.22 (m, 6H) 6.44 (s, 1H) 6.92 (d, J=8.79 Hz, 2H) 7.08 (d, J=8.50 Hz, 2H) 7.33 (d, J=4.98 Hz, 2H) 7.50 (d, J=7.62 Hz, 3H) 7.65 (s, 1H) 8.06 (d, J=8.20 Hz, 2H).

Compounds 2 through 6 were prepared in a similar manner to the method described in Example 1. The starting materials and the results are tabulated below in Table 1 for each case.

TABLE 1

| Compound number | IUPAC name | Starting material | $^1$ NMR (Solvent; δ ppm) |
|---|---|---|---|
| 2 | 1-(4-{5-[(3-chlorophenyl)(3,4-dimethylphenoxy)methyl]-1,2,4-oxadiazol-3-yl}benzyl)azetidine-3-carboxylic acid | 4-{5-[(3-chlorophenyl)(3,4-dimethylphenoxy)methyl]-1,2,4-oxadiazol-3-yl}benzaldehyde | $^1$H NMR (300 MHz, CDCl$_3$) δ ppm 2.15 (s, 3 H) 2.19 (s, 3 H) 3.26-3.42 (m, 1 H) 3.81-3.95 (m, 2 H) 3.97-4.14 (m, 4 H) 6.43 (s, 1 H) 6.71 (dd, J = 8.35, 2.20 Hz, 1 H) 6.84 (d, J = 2.05 Hz, 1 H) 6.99 (d, J = 7.91 Hz, 1 H) 7.30-7.37 (m, 2 H) 7.45-7.54 (m, 3 H) 7.65 (s, 1 H) 8.06 (d, J = 7.91 Hz, 2 H). |
| 3 | 1-(4-{5-[(3-chlorophenyl)(4-propylphenoxy)methyl]-1,2,4-oxadiazol-3-yl}benzyl)azetidine-3-carboxylic acid | 4-{5-[(3-Chlorophenyl)(4-propylphenoxy)methyl]-1,2,4-oxadiazol-3-yl}benzaldehyde | $^1$H NMR (300 MHz, CDCl$_3$) δ ppm 0.89 (t, J = 7.33 Hz, 3 H) 1.47-1.69 (m, 2 H) 2.49 (t, J = 7.62 Hz, 2 H) 3.35 (m, 1 H) 3.91 (t, J = 8.79 Hz, 2 H) 3.98-4.17 (m, 4 H) 6.44 (s, 1 H) 6.91 (d, J = 8.50 Hz, 2 H) 7.06 (d, J = 8.50 Hz, 2 H) 7.33 (d, J = 4.98 Hz, 2 H) 7.50 (d, J = 7.62 Hz, 3 H) 7.65 (s, 1 H) 8.06 (d, J = 7.91 Hz, 2 H). |
| 4 | 1-(4-{5-[(2-chlorophenyl)(3,4-dimethylphenoxy)methyl]-1,2,4-oxadiazol-3-yl}benzyl)azetidine-3-carboxylic acid | 4-{5-[(2-Chlorophenyl)(3,4 dimethylphenoxy)methyl]-1,2,4-oxadiazol-3-yl}benzaldehyde | $^1$H NMR (300 MHz, CDCl$_3$) δ ppm 2.15 (s, 3 H) 2.19 (s, 3 H) 3.35 (m, 1 H) 3.83-4.05 (m, 4 H) 4.10 (br. s., 2 H) 6.71 (dd, J = 8.06, 2.20 Hz, 1 H) 6.84 (d, J = 2.05 Hz, 1 H) 6.89 (s, 1 H) 6.99 (d, J = 8.20 Hz, 1 H) 7.31 (dt, J = 6.23, 3.19 Hz, 2 H) 7.36-7.44 (m, 1 H) 7.48 (d, J = 7.91 Hz, 2 H) 7.78-7.86 (m, 1 H) 8.05 (d, J = 8.20 Hz, 2 H). |

TABLE 1-continued

| Compound number | IUPAC name | Starting material | $^1$ NMR (Solvent; δ ppm) |
|---|---|---|---|
| 5 | 1-(4-{5-[(3-chlorophenyl)(4-methylphenoxy)methyl]-1,2,4-oxadiazol-3-yl}benzyl)azetidine-3-carboxylic acid | 4-{5-[(3-chlorophenyl)(4-methylphenoxy)methyl]-1,2,4-oxadiazol-3-yl}benzaldehyde, | $^1$H NMR (300 MHz, CDCl$_3$) δ ppm 2.25 (s, 3 H) 3.20-3.43 (m, 1 H) 3.90 (t, J = 8.94 Hz, 2 H) 3.99-4.16 (m, 4 H) 6.43 (s, 1 H) 6.90 (d, J = 8.50 Hz, 2 H) 7.01-7.11 (m, 2 H) 7.33 (d, J = 4.40 Hz, 2 H) 7.51 (d, J = 8.50 Hz, 3 H) 7.65 (s, 1 H) 8.06 (d, J = 7.91 Hz, 2 H). |
| 6 | 1-[4-(5-{(3-chlorophenyl)[(3,4-dimethylphenyl)amino]methyl}-1,2,4-oxadiazol-3-yl)benzyl]azetidine-3-carboxylic acid | 4-(5-{(3-chlorophenyl)[(3,4-dimethylphenyl)amino]methyl}-1,2,4-oxadiazol-3-yl)benzaldehyde, azetidine-3-carboxylic acid | $^1$H NMR (300 MHz, CDCl$_3$) δ ppm 2.11 (s, 3 H) 2.15 (s, 3 H) 3.37 (br. s., 1 H) 3.93 (br. s., 2 H) 3.98-4.21 (m, 4 H) 5.84 (s, 1 H) 6.40 (d, J = 8.50 Hz, 1 H) 6.51 (br. s., 1 H) 6.90 (d, J = 7.62 Hz, 1 H) 7.22-7.32 (m, 2 H) 7.40 (d, J = 3.22 Hz, 1 H) 7.52 (d, J = 8.79 Hz, 3 H) 8.05 (d, J = 7.62 Hz, 2 H) |

Biological Data

Compounds were synthesized and tested for S1P1 activity using the GTP γ$^{35}$S binding assay. These compounds may be assessed for their ability to activate or block activation of the human S1P1 receptor in cells stably expressing the S1P1 receptor.

GTP γ$^{35}$S binding was measured in the medium containing (mM) HEPES 25, pH 7.4, MgCl$_2$ 10, NaCl 100, dithitothreitol 0.5, digitonin 0.003%, 0.2 nM GTP γ$^{35}$S, and 5 μg membrane protein in a volume of 150 μl. Test compounds were included in the concentration range from 0.08 to 5,000 nM unless indicated otherwise. Membranes were incubated with 100 μM 5'-adenylylimmidodiphosphate for 30 min, and subsequently with 10 μM GDP for 10 min on ice. Drug solutions and membrane were mixed, and then reactions were initiated by adding GTP γ$^{35}$S and continued for 30 min at 25° C. Reaction mixtures were filtered over Whatman GF/B filters under vacuum, and washed three times with 3 mL of ice-cold buffer (HEPES 25, pH7.4, MgCl$_2$ 10 and NaCl 100). Filters were dried and mixed with scintillant, and counted for $^{35}$S activity using a β-counter. Agonist-induced GTP γ$^{35}$S binding was obtained by subtracting that in the absence of agonist. Binding data were analyzed using a non-linear regression method. In case of antagonist assay, the reaction mixture contained 10 nM S1P in the presence of test antagonist at concentrations ranging from 0.08 to 5000 nM.

Table 2 shows activity potency: S1P1 receptor from GTP γ$^{35}$S: nM, (EC$_{50}$).

Activity potency: S1P1 receptor from GTP γ$^{35}$S: nM, (EC$_{50}$),

TABLE 2

| IUPAC name | S1P1 EC$_{50}$ (nM) |
|---|---|
| 1-(4-{5-[(3-chlorophenyl)(4-ethylphenoxy)methyl]-1,2,4-oxadiazol-3-yl}benzyl)azetidine-3-carboxylic acid | 1060 |
| 1-(4-{5-[(3-chlorophenyl)(4-propylphenoxy)methyl]-1,2,4-oxadiazol-3-yl}benzyl)azetidine-3-carboxylic acid | 1100 |
| 1-(4-{5-[(3-chlorophenyl)(3,4-dimethylphenoxy)methyl]-1,2,4-oxadiazol-3-yl}benzyl)azetidine-3-carboxylic acid | 598 |
| 1-(4-{5-[(2-chlorophenyl)(3,4-dimethylphenoxy)methyl]-1,2,4-oxadiazol-3-yl}benzyl)azetidine-3-carboxylic acid | 911 |
| N-(1,3-benzodioxol-5-ylmethyl)-5-morpholin-4-yl-4-phenylthiophene-2-carboxamide | 336 |
| 1-[4-(5-{(3-chlorophenyl)[(3,4-dimethylphenyl)amino]methyl}-1,2,4-oxadiazol-3-yl)benzyl]azetidine-3-carboxylic acid | 312 |

What is claimed is:

1. A compound is presented by Formula I, its enantiomers, diastereoisomers, hydrates, tautomers or a pharmaceutically acceptable salt thereof, Formula I

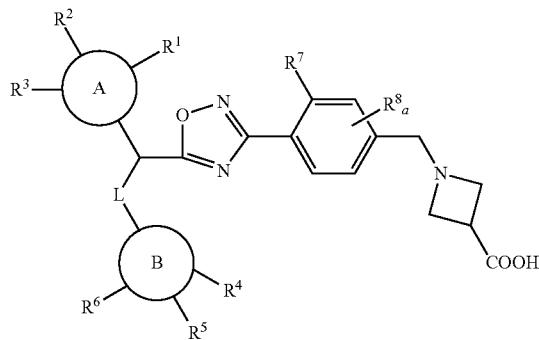

wherein:
A is $C_{6-10}$ aryl, heterocycle, $C_{3-8}$ cycloalkyl or $C_{3-8}$ cycloalkenyl;
B is $C_{6-10}$ aryl, heterocycle, $C_{3-8}$ cycloalkyl or $C_{3-8}$ cycloalkenyl;
$R^1$ is H, halogen, —$OC_{1-8}$ alkyl, $C_{1-8}$ alkyl, CN, $C(O)R^9$, $NR^{10}R^{11}$ or hydroxyl;
$R^2$ is H, halogen, —$OC_{1-8}$ alkyl, $C_{1-8}$ alkyl, CN, $C(O)R^9$, $NR^{10}R^{11}$ or hydroxyl;
$R^3$ is H, halogen, —$OC_{1-8}$ alkyl, $C_{1-8}$ alkyl, CN, $C(O)R^9$, $NR^{10}R^{11}$ or hydroxyl;
$R^4$ is H, halogen, —$OC_{1-8}$ alkyl, $C_{1-8}$ alkyl, CN, $C(O)R^9$, $NR^{10}R^{11}$ or hydroxyl;
$R^5$ is H, halogen, —$OC_{1-8}$ alkyl, $C_{1-8}$ alkyl, CN, $C(O)R^9$, $NR^{10}R^{11}$ or hydroxyl;
$R^6$ is H, halogen, —$OC_{1-8}$ alkyl, $C_{1-8}$ alkyl, CN, $C(O)R^9$, $NR^{10}R^{11}$ or hydroxyl;
$R^7$ is H, halogen, —$OC_{1-8}$ alkyl, $C_{1-8}$ alkyl, CN, $C(O)R^9$, $NR^{10}R^{11}$ or hydroxyl;
$R^8$ is halogen, —$OC_{1-8}$ alkyl, $C_{1-8}$ alkyl, CN, $C(O)R^9$, $NR^{10}R^{11}$ or hydroxyl;
L is O, S or NH;
$R^9$ is H, hydroxyl or $C_{1-8}$ alkyl;
$R^{10}$ is H or $C_{1-8}$ alkyl;
$R^{11}$ is H or $C_{1-8}$ alkyl; and
a is 0 or 1.

2. A compound according to claim 1 wherein:

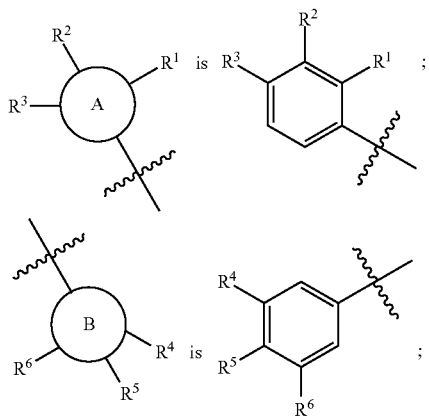

$R^1$ is H, halogen, —$OC_{1-6}$ alkyl, $C_{1-6}$ alkyl, CN, $C(O)R^9$, $NR^{10}R^{11}$ or hydroxyl;
$R^2$ is H, halogen, —$OC_{1-6}$ alkyl, $C_{1-6}$ alkyl, CN, $C(O)R^9$, $NR^{10}R^{11}$ or hydroxyl;
$R^3$ is H, halogen, —$OC_{1-6}$ alkyl, $C_{1-6}$ alkyl, CN, $C(O)R^9$, $NR^{10}R^{11}$ or hydroxyl;
$R^4$ is H, halogen, —$OC_{1-6}$ alkyl, $C_{1-6}$ alkyl, CN, $C(O)R^9$, $NR^{10}R^{11}$ or hydroxyl;
$R^5$ is H, halogen, —$OC_{1-6}$ alkyl, $C_{1-6}$ alkyl, CN, $C(O)R^9$, $NR^{10}R^{11}$ or hydroxyl;
$R^6$ is H, halogen, —$OC_{1-6}$ alkyl, $C_{1-6}$ alkyl, CN, $C(O)R^9$, $NR^{10}R^{11}$ or hydroxyl;
$R^7$ is H, halogen, —$OC_{1-6}$ alkyl, $C_{1-6}$ alkyl, CN, $C(O)R^9$, $NR^{10}R^{11}$ or hydroxyl;
$R^8$ is halogen, —$OC_{1-6}$ alkyl, $C_{1-6}$ alkyl, CN, $C(O)R^9$, $NR^{10}R^{11}$ or hydroxyl;
L is O, S or NH;
$R^9$ is H, hydroxyl or $C_{1-6}$ alkyl;
$R^{10}$ is H or $C_{1-6}$ alkyl;
$R^{11}$ is H or $C_{1-6}$ alkyl; and
a is 0 or 1.

3. A compound according to claim 2 wherein:
$R^1$ is H or halogen;
$R^2$ is H or halogen;
$R^3$ is H or halogen;
$R^4$ is H or $C_{1-6}$ alkyl,
$R^5$ is H or $C_{1-6}$ alkyl;
$R^6$ is H or $C_{1-6}$ alkyl;
$R^7$ is H;
a is 0; and
L is O, S or NH.

4. A compound according to claim 3 wherein:
L is O.

5. A compound according to claim 3 wherein:
L is NH.

6. A compound according to claim 1 selected from:
1-(4-{5-[(3-chlorophenyl)(4-ethylphenoxy)methyl]-1,2,4-oxadiazol-3-yl}benzyl)azetidine-3-carboxylic acid;
1-(4-{5-[(3-chlorophenyl)(3,4-dimethylphenoxy)methyl]-1,2,4-oxadiazol-3-yl}benzyl)azetidine-3-carboxylic acid;
1-(4-{5-[(3-chlorophenyl)(4-propylphenoxy)methyl]-1,2,4-oxadiazol-3-yl}benzyl)azetidine-3-carboxylic acid;
1-(4-{5-[(2-chlorophenyl)(3,4-dimethylphenoxy)methyl]-1,2,4-oxadiazol-3-yl}benzyl)azetidine-3-carboxylic acid;
1-(4-{5-[(3-chlorophenyl)(4-methylphenoxy)methyl]-1,2,4-oxadiazol-3-yl}benzyl)azetidine-3-carboxylic acid; and
1-[4-(5-{(3-chlorophenyl)[(3,4-dimethylphenyl)amino]methyl}-1,2,4-oxadiazol-3-yl)benzyl]azetidine-3-carboxylic acid.

7. A pharmaceutical composition comprising as active ingredient a therapeutically effective amount of a compound according to claim 1 and a pharmaceutically acceptable adjuvant, diluent or carrier.

8. A pharmaceutical composition according to claim 7 wherein the compound is selected from:
1-(4-{5-[(3-chlorophenyl)(4-ethylphenoxy)methyl]-1,2,4-oxadiazol-3-yl}benzyl)azetidine-3-carboxylic acid;
1-(4-{5-[(3-chlorophenyl)(3,4-dimethylphenoxy)methyl]-1,2,4-oxadiazol-3-yl}benzyl)azetidine-3-carboxylic acid;
1-(4-{5-[(3-chlorophenyl)(4-propylphenoxy)methyl]-1,2,4-oxadiazol-3-yl}benzyl)azetidine-3-carboxylic acid;
1-(4-{5-[(2-chlorophenyl)(3,4-dimethylphenoxy)methyl]-1,2,4-oxadiazol-3-yl}benzyl)azetidine-3-carboxylic acid;
1-(4-{5-[(3-chlorophenyl)(4-methylphenoxy)methyl]-1,2,4-oxadiazol-3-yl}benzyl)azetidine-3-carboxylic acid; and
1-[4-(5-{(3-chlorophenyl)[(3,4-dimethylphenyl)amino]methyl}-1,2,4-oxadiazol-3-yl)benzyl]azetidine-3-carboxylic acid.

* * * * *

UNITED STATES PATENT AND TRADEMARK OFFICE
CERTIFICATE OF CORRECTION

PATENT NO. : 8,501,726 B2
APPLICATION NO. : 13/293687
DATED : August 6, 2013
INVENTOR(S) : Wenkui K. Fang et al.

It is certified that error appears in the above-identified patent and that said Letters Patent is hereby corrected as shown below:

On the Title page, in Item (56), under "Other Publications", in column 2, line 4, delete "Nomencalture" and insert -- Nomenclature --, therefor.

On the Title page, in Item (56), under "Other Publications", in column 2, line 16, delete "Thoughput" and insert -- Throughput --, therefor.

In the Specification

In column 1, line 24, delete "Sphingosine-1 phosphate" and insert -- Sphingosine-1-phosphate --, therefor.

In column 2, line 23, delete "$C_{1-8}$alkyl," and insert -- $C_{1-8}$ alkyl, --, therefor.

In column 2, line 53, delete "wherein" and insert -- wherein: --, therefor.

In column 3, line 10, delete "wherein" and insert -- wherein: --, therefor.

In column 3, line 33, delete "alkyl," and insert -- alkyl; --, therefor.

In column 3, line 62, delete "alkyl," and insert -- alkyl; --, therefor.

In column 4, line 2, delete "wherein" and insert -- wherein: --, therefor.

In column 4, line 26, delete "alkyl," and insert -- alkyl; --, therefor.

In column 4, line 36, delete "wherein" and insert -- wherein: --, therefor.

In column 4, line 60, delete "alkyl," and insert -- alkyl; --, therefor.

In column 5, line 65, delete "chloro," and insert -- chloro; --, therefor.

In column 10, line 27, delete "Stahal" and insert -- Stahl --, therefor.

In column 10, line 28, delete "Chemica" and insert -- Chimica --, therefor.

In column 11, line 5, delete "immnuosuppression:" and insert -- immunosuppression: --, therefor.

In column 11, line 8, delete "antoimmune" and insert -- autoimmune --, therefor.

In column 11, line 10, delete "dermititis," and insert -- dermatitis, --, therefor.

Signed and Sealed this
Tenth Day of December, 2013

Margaret A. Focarino
*Commissioner for Patents of the United States Patent and Trademark Office*

In column 12, line 1, delete "immnuosuppression:" and insert -- immunosuppression: --, therefor.

In column 12, line 4, delete "antoimmune" and insert -- autoimmune --, therefor.

In column 12, line 6, delete "dermititis," and insert -- dermatitis, --, therefor.

In column 14, line 61, delete "Burlier," and insert -- Burrier, --, therefor.

In column 14, line 61, delete "Ciader," and insert -- Clader, --, therefor.

In column 16, line 23, delete "diasteroisomeric" and insert -- diastereoisomeric --, therefor.

In column 17, line 2, delete "benzaldehyde,)," and insert -- benzaldehyde), --, therefor.

In columns 17-18, lines 2-3 Compound 4 (Table 1), delete "(3,4 dimethylphenoxy)" and insert -- (3,4-dimethylphenoxy) --, therefor.

In columns 19-20, line 6 Compound 5 (Table 1-continued), delete "benzaldehyde," and insert -- benzaldehyde --, therefor.

In columns 19-20, lines 2-3 Compound 6 (Table 1-continued), delete "[(3,4 dimethylphenyl)" and insert -- [(3,4-dimethylphenyl) --, therefor.

In column 19, lines 46-47, delete "dithitothreitol" and insert -- dithiothreitol --, therefor.

In column 19, line 52, delete "5'-adenylylimmidodiphosphate" and insert -- 5'-adenylylimidodiphosphate --, therefor.

In the Claims

In column 21, line 22, in claim 1, delete "$C_{1-8}$alkyl," and insert -- $C_{1-8}$ alkyl, --, therefor.

In column 22, line 20, in claim 3, delete "alkyl," and insert -- alkyl; --, therefor.